US 8,597,365 B2

(12) United States Patent
Meridew

(10) Patent No.: US 8,597,365 B2
(45) Date of Patent: Dec. 3, 2013

(54) PATIENT-SPECIFIC PELVIC IMPLANTS FOR ACETABULAR RECONSTRUCTION

(75) Inventor: Jason D. Meridew, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 125 days.

(21) Appl. No.: 13/197,851

(22) Filed: Aug. 4, 2011

(65) Prior Publication Data

US 2013/0035766 A1 Feb. 7, 2013

(51) Int. Cl.
*A61F 2/32* (2006.01)
*A61F 2/34* (2006.01)

(52) U.S. Cl.
USPC ..................................... 623/22.32; 623/22.38

(58) Field of Classification Search
None
See application file for complete search history.

(56) References Cited

U.S. PATENT DOCUMENTS

| | | |
|---|---|---|
| 1,480,285 A | 1/1924 | Moore |
| 2,181,746 A | 11/1939 | Siebrandt |
| 2,407,845 A | 9/1946 | Nemeyer |
| 2,618,913 A | 11/1952 | Plancon et al. |
| 2,910,978 A | 11/1959 | Urist |
| 3,840,904 A | 10/1974 | Tronzo |
| 4,246,895 A | 1/1981 | Rehder |
| 4,306,866 A | 12/1981 | Weissman |
| 4,324,006 A | 4/1982 | Charnley |
| 4,421,112 A | 12/1983 | Mains et al. |
| 4,436,684 A | 3/1984 | White |
| 4,475,549 A | 10/1984 | Oh |
| 4,506,393 A | 3/1985 | Murphy |
| 4,524,766 A | 6/1985 | Petersen |
| 4,619,658 A | 10/1986 | Pappas et al. |
| 4,621,630 A | 11/1986 | Kenna |
| 4,632,111 A | 12/1986 | Roche |
| 4,633,862 A | 1/1987 | Petersen |
| 4,663,720 A | 5/1987 | Duret et al. |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,719,907 A | 1/1988 | Banko et al. |
| 4,721,104 A | 1/1988 | Kaufman et al. |
| 4,722,330 A | 2/1988 | Russell et al. |
| 4,778,474 A | 10/1988 | Homsy |
| 4,800,874 A | 1/1989 | David et al. |

(Continued)

FOREIGN PATENT DOCUMENTS

| | | |
|---|---|---|
| CA | 2447694 A1 | 12/2002 |
| CA | 2501041 A1 | 4/2004 |

(Continued)

OTHER PUBLICATIONS

Great Britain Search Report mailed Dec. 21, 2011 for GB1116054.6, claiming benefit of U.S. Appl. No. 12/888,005, filed Sep. 22, 2010.

(Continued)

*Primary Examiner* — David H Willse
*Assistant Examiner* — Javier Blanco
(74) *Attorney, Agent, or Firm* — Harness, Dickey

(57) ABSTRACT

A pelvic implant includes a first surface including a recess configured for receiving a portion of a flange of an acetabular cage and a patient-specific second surface opposite to the first surface. The patient-specific second surface is preoperatively configured from a three-dimensional digital image of a pelvis of a patient to mate and closely conform to a corresponding surface of the pelvis under the flange in only one position.

14 Claims, 10 Drawing Sheets

(56) References Cited

U.S. PATENT DOCUMENTS

Figure 1:
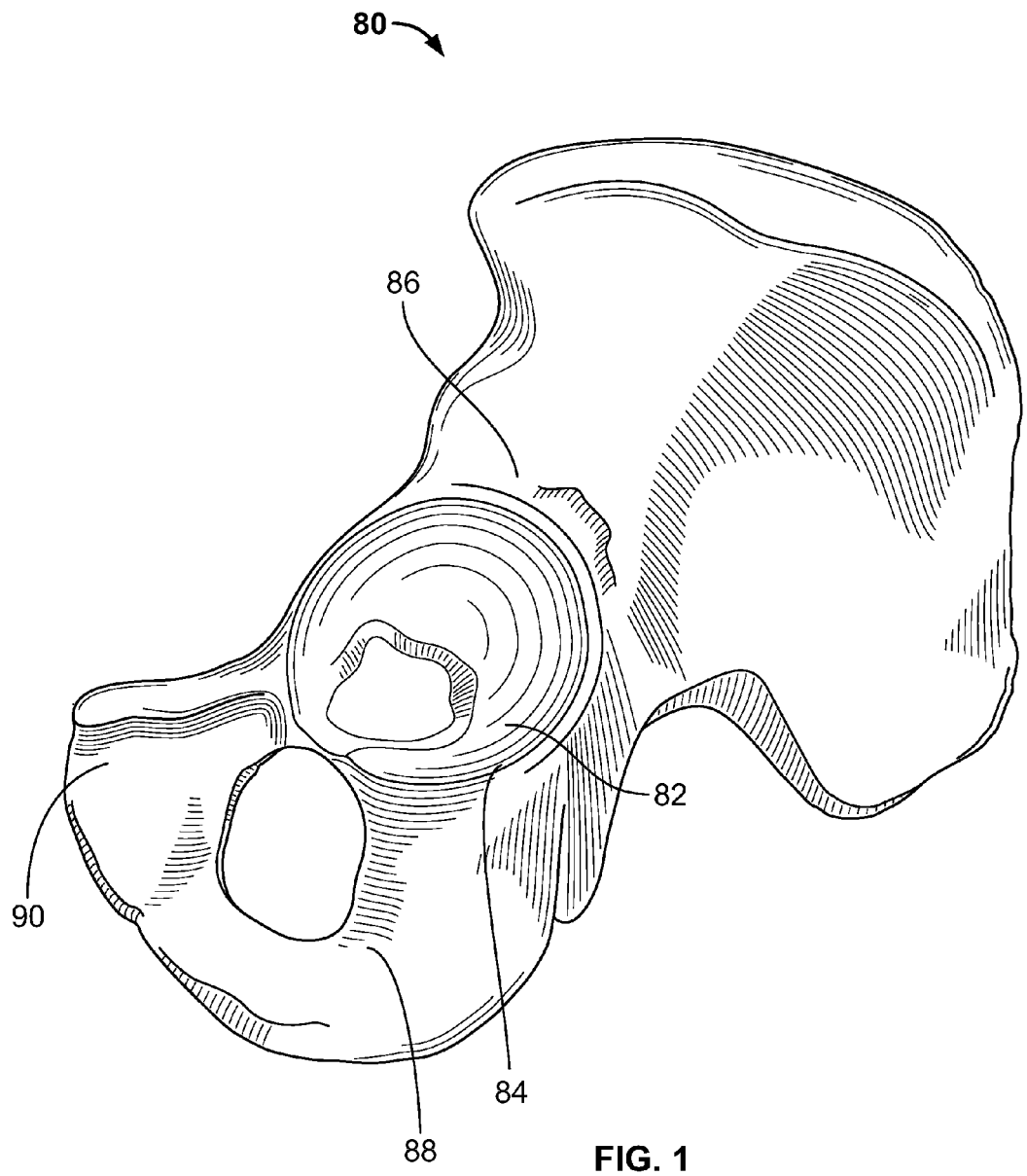

| | | |
|---|---|---|
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,893,619 A | 1/1990 | Dale et al. |
| 4,896,663 A | 1/1990 | Vandewalls |
| 4,927,422 A | 5/1990 | Engelhardt |
| 4,936,862 A | 6/1990 | Walker et al. |
| 4,952,213 A | 8/1990 | Bowman et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,002,579 A | 3/1991 | Copf et al. |
| 5,007,936 A | 4/1991 | Woolson |
| 5,019,105 A | 5/1991 | Wiley |
| 5,030,221 A | 7/1991 | Buechel et al. |
| 5,041,117 A | 8/1991 | Engelhardt |
| 5,053,037 A | 10/1991 | Lackey |
| 5,053,039 A | 10/1991 | Hofmann et al. |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,122,144 A | 6/1992 | Bert et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,150,304 A | 9/1992 | Berchem et al. |
| 5,176,684 A | 1/1993 | Ferrante et al. |
| 5,176,711 A | 1/1993 | Grimes |
| 5,246,444 A | 9/1993 | Schreiber |
| 5,258,032 A | 11/1993 | Bertin |
| 5,261,915 A | 11/1993 | Durlacher et al. |
| 5,274,565 A | 12/1993 | Reuben |
| 5,299,288 A | 3/1994 | Glassman et al. |
| 5,300,077 A | 4/1994 | Howell |
| 5,320,625 A | 6/1994 | Bertin |
| 5,342,366 A | 8/1994 | Whiteside et al. |
| 5,344,423 A | 9/1994 | Dietz et al. |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,415,662 A | 5/1995 | Ferrante et al. |
| 5,417,694 A | 5/1995 | Marik et al. |
| 5,438,263 A | 8/1995 | Dworkin et al. |
| 5,440,496 A | 8/1995 | Andersson et al. |
| 5,448,489 A | 9/1995 | Reuben |
| 5,449,360 A | 9/1995 | Schreiber |
| 5,452,407 A | 9/1995 | Crook |
| 5,454,816 A | 10/1995 | Ashby |
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,540,695 A | 7/1996 | Levy |
| 5,549,688 A | 8/1996 | Ries et al. |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,595,703 A | 1/1997 | Swaelens et al. |
| 5,607,431 A | 3/1997 | Dudasik et al. |
| 5,613,969 A | 3/1997 | Jenkins, Jr. |
| 5,620,448 A | 4/1997 | Puddu |
| 5,634,927 A | 6/1997 | Houston et al. |
| 5,641,323 A | 6/1997 | Caldarise |
| 5,658,294 A | 8/1997 | Sederholm |
| 5,662,656 A | 9/1997 | White |
| 5,671,018 A | 9/1997 | Ohara et al. |
| 5,677,107 A | 10/1997 | Neckers |
| 5,681,354 A | 10/1997 | Eckhoff |
| 5,682,886 A | 11/1997 | Delp et al. |
| 5,690,635 A | 11/1997 | Matsen, III et al. |
| 5,702,460 A | 12/1997 | Carls et al. |
| 5,704,941 A | 1/1998 | Jacober et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,768,134 A | 6/1998 | Swaelens et al. |
| 5,769,092 A | 6/1998 | Williamson, Jr. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,879,404 A | 3/1999 | Bateman et al. |
| 5,880,976 A | 3/1999 | DiGioia, III et al. |
| 5,885,297 A | 3/1999 | Matsen, III |
| 5,885,298 A | 3/1999 | Herrington et al. |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,921,988 A | 7/1999 | Legrand |
| 5,925,049 A | 7/1999 | Gustilo et al. |
| 5,925,077 A | 7/1999 | Williamson et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,033,415 A | 3/2000 | Mittelstadt et al. |
| 6,059,789 A | 5/2000 | Dinger et al. |
| 6,059,833 A | 5/2000 | Doets |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,132,469 A | 10/2000 | Schroeder |
| 6,136,033 A | 10/2000 | Suemer |
| 6,156,069 A | 12/2000 | Amstutz |
| 6,161,080 A | 12/2000 | Aouni-Ateshian et al. |
| 6,187,010 B1 | 2/2001 | Masini |
| 6,195,615 B1 | 2/2001 | Lysen |
| 6,203,546 B1 | 3/2001 | MacMahon |
| 6,205,411 B1 | 3/2001 | DiGioia, III et al. |
| 6,206,927 B1 | 3/2001 | Fell et al. |
| 6,254,604 B1 | 7/2001 | Howell |
| 6,258,097 B1 | 7/2001 | Cook et al. |
| 6,264,698 B1 | 7/2001 | Lawes et al. |
| 6,273,891 B1 | 8/2001 | Masini |
| 6,290,727 B1 | 9/2001 | Otto et al. |
| 6,293,971 B1 | 9/2001 | Nelson et al. |
| 6,312,258 B1 | 11/2001 | Ashman |
| 6,312,473 B1 | 11/2001 | Oshida |
| 6,319,285 B1 | 11/2001 | Chamier et al. |
| 6,325,829 B1 | 12/2001 | Schmotzer |
| 6,343,987 B2 | 2/2002 | Hayama et al. |
| 6,354,011 B1 | 3/2002 | Albrecht |
| 6,379,299 B1 | 4/2002 | Borodulin et al. |
| 6,383,228 B1 | 5/2002 | Schmotzer |
| 6,391,251 B1 | 5/2002 | Keicher et al. |
| 6,395,005 B1 | 5/2002 | Lovell |
| 6,416,553 B1 | 7/2002 | White et al. |

(56) References Cited

U.S. PATENT DOCUMENTS

| | | |
|---|---|---|
| 6,427,698 B1 | 8/2002 | Yoon |
| 6,459,948 B1 | 10/2002 | Ateshian et al. |
| 6,463,351 B1 | 10/2002 | Clynch |
| 6,475,243 B1 | 11/2002 | Sheldon et al. |
| 6,482,236 B2 | 11/2002 | Habecker |
| 6,488,715 B1 | 12/2002 | Pope et al. |
| 6,503,255 B1 | 1/2003 | Albrektsson et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,591,581 B2 | 7/2003 | Schmieding |
| 6,605,293 B1 | 8/2003 | Giordano et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,682,566 B2 | 1/2004 | Draenert |
| 6,682,567 B1 | 1/2004 | Schroeder |
| 6,696,073 B2 | 2/2004 | Boyce et al. |
| 6,697,664 B2 | 2/2004 | Kienzle, III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladino |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,966,932 B1 | 11/2005 | Schroeder |
| 6,990,220 B2 | 1/2006 | Ellis et al. |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | McKinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| 7,169,185 B2 | 1/2007 | Sidebotham |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | DiSilvestro et al. |
| 7,220,264 B1 | 5/2007 | Hershberger |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,207 B1 | 2/2008 | Smith |
| 7,335,231 B2 | 2/2008 | McLean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,392,076 B2 | 6/2008 | Moctezuma de La Barrera |
| 7,427,200 B2 | 9/2008 | Noble et al. |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian |
| 7,494,510 B2 | 2/2009 | Zweymuller |
| 7,517,365 B2 | 4/2009 | Carignan et al. |
| 7,527,631 B2 | 5/2009 | Maroney et al. |
| 7,534,263 B2 | 5/2009 | Burdulis, Jr. et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-Schaffer et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,723,395 B2 | 5/2010 | Ringeisen et al. |
| 7,780,672 B2 | 8/2010 | Metzger et al. |
| 7,780,740 B2 | 8/2010 | Steinberg |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,879,109 B2 | 2/2011 | Borden et al. |
| 7,892,261 B2 | 2/2011 | Bonutti |
| 7,896,921 B2 | 3/2011 | Smith et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,993,353 B2 | 8/2011 | Rossner et al. |
| 8,062,301 B2 | 11/2011 | Ammann et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |

(56) References Cited

U.S. PATENT DOCUMENTS

| | | |
|---|---|---|
| 8,133,230 B2 | 3/2012 | Stevens et al. |
| 8,133,234 B2 | 3/2012 | Meridew et al. |
| 8,137,406 B2 | 3/2012 | Novak et al. |
| 8,167,951 B2 | 5/2012 | Ammann et al. |
| 8,170,641 B2 | 5/2012 | Belcher |
| 8,182,489 B2 | 5/2012 | Horacek |
| 8,192,441 B2 | 6/2012 | Collazo |
| 8,192,495 B2 | 6/2012 | Simpson et al. |
| 8,211,112 B2 | 7/2012 | Novak et al. |
| 8,241,292 B2 | 8/2012 | Collazo |
| 8,241,293 B2 | 8/2012 | Stone et al. |
| 8,265,790 B2 | 9/2012 | Amiot et al. |
| 8,282,646 B2 | 10/2012 | Schoenefeld et al. |
| 8,298,237 B2 | 10/2012 | Schoenefeld et al. |
| 8,303,596 B2 | 11/2012 | Plaβky et al. |
| 8,333,772 B2 | 12/2012 | Fox et al. |
| 8,355,773 B2 | 1/2013 | Leitner et al. |
| 2001/0005797 A1 | 6/2001 | Barlow et al. |
| 2001/0011190 A1 | 8/2001 | Park |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0107522 A1 | 8/2002 | Picard et al. |
| 2002/0120342 A1 | 8/2002 | Gibbs |
| 2002/0128872 A1 | 9/2002 | Giammattei |
| 2002/0147415 A1 | 10/2002 | Martelli |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0212459 A1 | 11/2003 | Gibbs |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0220583 A1 | 11/2004 | Pieczynski et al. |
| 2004/0225369 A1 | 11/2004 | Lakin et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0021148 A1 | 1/2005 | Gibbs |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0216305 A1 | 9/2005 | Funderud |
| 2005/0222573 A1 | 10/2005 | Branch et al. |
| 2005/0228393 A1 | 10/2005 | Williams et al. |
| 2005/0234461 A1 | 10/2005 | Burdulis et al. |
| 2005/0234465 A1 | 10/2005 | McCombs et al. |
| 2005/0234468 A1 | 10/2005 | Carson |
| 2005/0240195 A1 | 10/2005 | Axelson et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0142657 A1 | 6/2006 | Quaid et al. |
| 2006/0155380 A1 | 7/2006 | Clemow et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0195111 A1 | 8/2006 | Couture |
| 2006/0195194 A1 | 8/2006 | Gunther |
| 2006/0195198 A1 | 8/2006 | James |

(56) References Cited

U.S. PATENT DOCUMENTS

| | | |
|---|---|---|
| 2006/0198943 A1 | 9/2006 | Kumar |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0293681 A1 | 12/2006 | Claypool et al. |
| 2007/0015995 A1 | 1/2007 | Lang et al. |
| 2007/0016209 A1 | 1/2007 | Ammann et al. |
| 2007/0027680 A1 | 2/2007 | Ashley et al. |
| 2007/0066917 A1 | 3/2007 | Hodorek et al. |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106391 A1 | 5/2007 | Ronk |
| 2007/0118055 A1 | 5/2007 | McCombs |
| 2007/0118138 A1 | 5/2007 | Seo et al. |
| 2007/0118243 A1 | 5/2007 | Schroeder et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1 | 8/2007 | Lang et al. |
| 2007/0203430 A1 | 8/2007 | Lang et al. |
| 2007/0203583 A1 | 8/2007 | Slone |
| 2007/0203605 A1 | 8/2007 | Melton et al. |
| 2007/0219562 A1 | 9/2007 | Slone et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0244487 A1 | 10/2007 | Ammann et al. |
| 2007/0250169 A1 | 10/2007 | Lang |
| 2007/0250175 A1 | 10/2007 | Meridew et al. |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009874 A1 | 1/2008 | Meridew et al. |
| 2008/0009952 A1 | 1/2008 | Hodge |
| 2008/0015599 A1 | 1/2008 | D'Alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0021299 A1 | 1/2008 | Meulink |
| 2008/0021494 A1 | 1/2008 | Schmelzeisen-Redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0221699 A1 | 9/2008 | Meridew et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262500 A1 | 10/2008 | Collazo |
| 2008/0262624 A1 | 10/2008 | White et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0294170 A1 | 11/2008 | O'Brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0043556 A1 | 2/2009 | Axelson et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |

(56) References Cited

U.S. PATENT DOCUMENTS

| | | |
|---|---|---|
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0118736 A1 | 5/2009 | Kreuzer |
| 2009/0118769 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0204225 A1 | 8/2009 | Meridew et al. |
| 2009/0209884 A1 | 8/2009 | Van Vorhis et al. |
| 2009/0209961 A1 | 8/2009 | Ferrante et al. |
| 2009/0210067 A1 | 8/2009 | Meridew |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez |
| 2009/0234360 A1 | 9/2009 | Alexander |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1 | 1/2010 | Dower |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0042105 A1 | 2/2010 | Park et al. |
| 2010/0049195 A1 | 2/2010 | Park et al. |
| 2010/0049327 A1 | 2/2010 | Isch et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0087829 A1 | 4/2010 | Metzger et al. |
| 2010/0094295 A1 | 4/2010 | Schnieders et al. |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0131073 A1 | 5/2010 | Meridew et al. |
| 2010/0136214 A1 | 6/2010 | Kumar |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0145466 A1 | 6/2010 | Slone |
| 2010/0152782 A1 | 6/2010 | Stone et al. |
| 2010/0160917 A1 | 6/2010 | Fitz et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198224 A1 | 8/2010 | Metzger et al. |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0286789 A1 | 11/2010 | Meridew |
| 2010/0292743 A1 | 11/2010 | Singhal et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0009869 A1 | 1/2011 | Marino et al. |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0015753 A1 | 1/2011 | Meridew |
| 2011/0022049 A1 | 1/2011 | Huebner et al. |
| 2011/0029091 A1 | 2/2011 | Bojarski et al. |
| 2011/0029116 A1 | 2/2011 | Jordan et al. |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0092804 A1 | 4/2011 | Schoenefeld et al. |
| 2011/0093086 A1 | 4/2011 | Witt et al. |
| 2011/0106254 A1 | 5/2011 | Abel et al. |
| 2011/0125264 A1 | 5/2011 | Bagga et al. |
| 2011/0130795 A1 | 6/2011 | Ball |
| 2011/0151027 A1 | 6/2011 | Clineff et al. |
| 2011/0151259 A1 | 6/2011 | Jarman-Smith et al. |
| 2011/0153025 A1 | 6/2011 | McMinn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0184424 A1 | 7/2011 | Isch et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2011/0275032 A1 | 11/2011 | Tardieu et al. |
| 2011/0295887 A1 | 12/2011 | Palmese et al. |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0065640 A1 | 3/2012 | Metzger et al. |
| 2012/0078259 A1 | 3/2012 | Meridew |
| 2012/0089595 A1 | 4/2012 | Jaecksch |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0130382 A1 | 5/2012 | Iannotti et al. |
| 2012/0136365 A1 | 5/2012 | Iannotti et al. |

(56) References Cited

U.S. PATENT DOCUMENTS

| | | | |
|---|---|---|---|
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0209276 A1 | 8/2012 | Schuster |
| 2012/0215225 A1 | 8/2012 | Philippon et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0259335 A1 | 10/2012 | Scifert et al. |
| 2012/0265208 A1 | 10/2012 | Smith |
| 2012/0271314 A1 | 10/2012 | Stemniski et al. |
| 2012/0271366 A1 | 10/2012 | Katrana et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2013/0001121 A1 | 1/2013 | Metzger |
| 2013/0006250 A1 | 1/2013 | Metzger et al. |
| 2013/0035766 A1 | 2/2013 | Meridew |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 3447365 A1 | 7/1986 |
| DE | 04219939 | 12/1993 |
| DE | 4421153 A1 | 12/1995 |
| DE | 102009028503 A | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1634551 A2 | 3/2006 |
| EP | 1852072 A2 | 7/2007 |
| EP | 1832239 A1 | 9/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| FR | 2659226 A1 | 9/1991 |
| FR | 2721195 A1 | 12/1995 |
| FR | 2768916 A1 | 4/1999 |
| GB | 2094590 A | 9/1982 |
| GB | 2197790 A | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 11/1985 |
| JP | 2011505080 A | 2/2011 |
| JP | 2011527885 A | 11/2011 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-02026145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010144705 A1 | 12/2010 |
| WO | WO-2010148103 A1 | 12/2010 |
| WO | WO-2011018458 A1 | 2/2011 |
| WO | WO-2011041398 A1 | 4/2011 |
| WO | WO-2011060536 A1 | 5/2011 |
| WO | WO-2011019797 A3 | 7/2011 |
| WO | WO-2011106711 A1 | 9/2011 |
| WO | WO-2011109260 A1 | 9/2011 |

(56) References Cited

FOREIGN PATENT DOCUMENTS

| WO | WO-2011110374 A1 | 9/2011 |
|---|---|---|
| WO | WO-2012006444 A2 | 1/2012 |
| WO | WO-2012033821 A1 | 3/2012 |
| WO | WO-2012058344 A1 | 5/2012 |
| WO | WO-2012061042 A1 | 5/2012 |
| WO | WO-2012058353 A4 | 6/2012 |
| WO | WO-2012058355 A4 | 7/2012 |
| WO | WO-2012058349 A4 | 8/2012 |
| WO | WO-2012116206 A1 | 8/2012 |
| WO | WO-2012158917 A1 | 11/2012 |
| WO | WO-2012173929 A1 | 12/2012 |
| WO | WO-2012174008 A1 | 12/2012 |

OTHER PUBLICATIONS

International Preliminary Report and Written Opinion mailed Jan. 5, 2012 for PCT/US2010/038845 claiming benefit of U.S. Appl. No. 12/486,992, filed Jun. 18, 2009.

International Preliminary Report on Patentability and Written Opinion mailed Dec. 22, 2011 for PCT/US2010/038177 claiming benefit of U.S. Appl. No. 12/483,807, filed Jun. 12, 2009.

International Search Report mailed Nov. 30, 2010 for PCT/EP2010/061630 filed Aug. 10, 2010 claiming benefit of DE102009028503.2 filed Aug. 13, 2009.

Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.

"Comprehensive® Reverse Shoulder System Surgical Technique," Biomet Orthopedics brochure (2009-2012), 48 pages.

"Comprehensive® Reverse Shoulder System Technical Design Features," Biomet Orthopedics brochure (2009), 3 pages.

"Comprehensive® Reverse Shoulder System," Biomet Orthopedics brochure (2009), 8 pages.

"Comprehensive® Shoulder System Surgical Technique," Biomet Orthopedics brochure (2007), pp. 1-53.

"Comprehensive® Total Shoulder System," Biomet Orthopedics brochure (2011), 4 pages.

Friedman, R.J. et al., "The Use of Computerized Tomography in the Measurement of Glenoid Version", Journal of Bone & Joint Surgery Am. (JBJS) 1992;74:1032-1037 (Aug. 1992).

International Search Report and Written Opinion mailed Dec. 18, 2012 for PCT/US2012/059189, which claims benefit of U.S. Appl. No. 13/597,478 filed Aug. 29, 2011.

International Search Report and Written Opinion mailed Feb. 6, 2013 for PCT/US2012/060842, which claims benefit of U.S. Appl. No. 13/653,868 filed Oct. 17, 2012.

International Search Report and Written Opinion mailed Feb. 6, 2013 for PCT/US2012/060854, which claims benefit of U.S. Appl. No. 13/653,893, filed Oct. 17, 2012.

International Search Report and Written Opinion mailed Nov. 15, 2012, for PCT/US2012/052853, which claims benefit of U.S. Appl. No. 13/221,968, filed Aug. 31, 2011.

International Search Report mailed Oct. 23, 2012, for PCT/US2012/041893, which claims benefit of U.S. Appl. No. 61/496,177, filed Jun. 13, 2011.

Invitation to Pay Additional Fees mailed Feb. 6, 2013 for PCT/US2012/060848, which claims benefit of U.S. Appl. No. 13/653,878, filed Oct. 17, 2012.

Invitation to Pay Additional Fees mailed Feb. 7, 2013 for PCT/US2012/060853, which claims benefit of U.S. Appl. No. 13/653,893, filed Oct. 17, 2012.

Biomet "Oxford® Partial Knee" brochure, 8 pages (Feb. 2011).

Biomet "The Oxford® Partial Knee Surgical Technique," brochure, pp. 1-38, (Feb. 2010).

Biomet, "Oxford® Partial Knee Microplasty® Instrumentation Surgical Technique", brochure, pp. 1-54 (May 2011).

International Preliminary Report on Patentability and Written Opinion mailed Sep. 7, 2012 for PCT/US2011/026333 claiming benefit of U.S. Appl. No. 12/714,023, filed Feb. 26, 2010.

International Preliminary Report on Patentability for PCT/US2010/050701 mailed Apr. 12, 2012 claiming benefit of U.S. Appl. No. 12/571,969, filed Oct. 1, 2009.

International Search Report and Written Opinion mailed Mar. 5, 2012 for PCT/US2011/057300 claiming benefit of U.S. Appl. No. 12/938,905, filed Nov. 3, 2010.

International Search Report and Written Opinion mailed May 8, 2012 for PCT/US2012/026356 claiming benefit of U.S. Appl. No. 13/041,883, filed Mar. 7, 2011.

Thoma, W., et al., "Endoprothetischen Versorgung des Kniegelenks auf der Basis eines 3D-computertomographischen Subtraktionsverfahrens," Zuma Thema: Computergestützte orthopädische Chirugie, Der Orthopäde 29:641-644 Springer-Verlag (Jul. 2000) Translation provided: Thoma, W., "Endoprosthetic care of the knee joint based on a 3D computer chromatography subtraction process," Topic: Computer-aided orthopedic surgery. Orthopedist 2000 29:641-644 Springer Verlag (Jul. 2000).

"Amazing Precision. Beautiful Results. The next evolution of MAKOplasty® is here," brochure. (Feb. 2009) MAKO Surgical Corp. 6 pages.

"Ascent Total Knee System," brochure. Biomet, Inc. (1999) 16 sheets.

"Customized Patient Instruments, Patient specific instruments for patient specific needs," brochure. (2008) DePuy Orthopaedics, Inc. 14 sheets.

"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.

"Discovery® Elbow System Surgical Technique," brochure. Biomet Orthopedics, Inc. (2008) pp. 1-25.

"Discovery® Elbow System," brochure. Biomet Orthopedics, Inc. (2007) 3 sheets.

"Hipsextant Instructions of Use." (2011) Surgical Planning Associates, Inc. 19 pages.

"Knee tensor combined with laser femoral head locator," Research Disclosure. Jul. 2006. No. 507; p. 903.

"Max-Ti™, Modular Protrusio Cage," Surgical Technique brochure. Biomet Orthopedics, Inc. (2003) 10 sheets.

"Max-Ti™ Modular Protrusio Cage," Surgical Technique brochure. Biomet Orthopedics, Inc. (2006) 12 sheets.

"Method for constructing an allograft sleeve." Research Disclosure (Dec. 2003) No. 476, p. 1294.

"OSS™ Orthopaedic Salvage System, Femoral/Tibial Augmentation," brochure. Biomet Orthopedics, Inc., (2003) pp. 1-8 (12 sheets).

"PAR 5™ Protrusio Acetabular Reconstruction System," brochure. (2006) Biomet Orthopedics, Inc. 12 sheets.

"Patient Matched PMI Implants, C.A.M.R.A. 3-D Imaging," brochure, Biomet, Inc. (1990) 6 pages.

"Regenerex® Tibial Cone Augment, Surgical Technique Addendum to the Vanguard® SSK Revision System," brochure. Biomet® Orthopedics. (2009) pp. 1-8 (12 sheets).

"Signature™ Personalized Patient Care, Surgical Technique Addendum to the Vanguard Knee System" brochure. Biomet® Orthopedics, Inc. (2009) pp. 1-8.

"TruMatch™ Personalized knee replacement solutions," tri-fold brochure. (2009) SIGMA® DePuy Orthopaedics, Inc. 2 pages.

"Vanguard® PFR Partial Knee Patellofemoral Replacement System," Surgical Technique brochure. Biomet Orthopaedics, (2010) pp. 1-25.

"Zimmer® UniSpacer® Knee System," brochure. (2005) Zimmer, Inc. 4 sheets.

Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.

Botha, Chad P., Technical Report: DeVIDE—The Delft Visualisation and Image processing Development Environment, pp. 1-49 (May 31, 2006).

Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.

(56) References Cited

OTHER PUBLICATIONS

Eckhoff, Donald G., et al., "Three-Dimentional Mechanics, Kinematics, and Morphology of the Knee Viewed in Virtual Reality," The Journal of Bone & Joint Surgery, vol. 81 (Dec. 4, 2005) pp. 71-80.
Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.
Haaker, R.G., et al., "Minimal-invasive navigiert implantierte unikondyläre Knieendoprothese," Orthopäde 2006 35:1073-1079 (2006) Spinger Medizin Verlag.
Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.
Hazan, Eric J., M.D., "Computer-Assisted Orthopaedic Sugery, A New Paradigm," Techniques in Orthopaedics® vol. 18, No. 2, (2003) pp. 221-229.
Hutmacher, Dietmar, W., "Scaffolds in tissue engineering bone and cartilage," Biomaterials, 2000 Elsevier Science Ltd. (pp. 2529-2543).
International Preliminary Report on Patentability and Written Opinion for PCT/US2009/039578 mailed Oct. 28, 2010 claiming benefit of U.S. Appl. No. 12/103,834, filed Apr. 16, 2008.
International Preliminary Report on Patentability and Written Opinion mailed Oct. 28, 2010 for PCT/US2009/039507 claiming benefit of U.S. Appl. No. 12/103,824, filed Apr. 16, 2008.
International Preliminary Report on Patentability for PCT/US2007/013223 mailed Dec. 24, 2008 claiming benefit of U.S. Appl. No. 11/756,057, filed May 31, 2007.
International Preliminary Report on Patentability mailed Aug. 25, 2011 for PCT/US2010/024073 filed Feb. 12, 2010, claiming benefit of U.S. Appl. No. 12/371,096, filed Feb. 13, 2009.
International Preliminary Report on Patentability mailed Mar. 31, 2011 for PCT/US2009/056670 claiming benefit of U.S. Appl. No. 12/211,407, filed Sep. 16, 2008.
International Preliminary Report on Patentability mailed Sep. 1, 2011 for PCT/US2010/024579 claiming benefit of U.S. Appl. No. 12/389,930, filed Feb. 20, 2009.
International Preliminary Report on Patentability mailed Sep. 1, 2011 for PCT/US2010/024584 claiming benefit of U.S. Appl. No. 12/389,901, filed Feb. 20, 2009.
International Search Report and Written Opinion for PCT/US2007/013223 mailed Nov. 26, 2007, claiming benefit of U.S. Appl. No. 11/756,057, filed May 31, 2007.
International Search Report and Written Opinion for PCT/US2009/039507 mailed Jul. 14, 2009, claiming benefit of U.S. Appl. No. 12/103,824.
International Search Report and Written Opinion for PCT/US2009/056670 mailed Mar. 2, 2010 claiming benefit of U.S. Appl. No. 12/211,407, filed Sep. 16, 2008.
International Search Report and Written Opinion mailed Apr. 22, 2010 for PCT/US2010/024579 claiming benefit of U.S. Appl. No. 12/389,930, filed Feb. 20, 2009.
International Search Report and Written Opinion mailed Aug. 19, 2010 for PCT/US2010/024584 claiming benefit of U.S. Appl. No. 12/389,901, filed Feb. 20, 2009.
International Search Report and Written Opinion mailed Aug. 9, 2011 for PCT/US2011/026333 claiming benefit of U.S. Appl. No. 12/714,023, filed Feb. 26, 2010.
International Search Report and Written Opinion mailed Dec. 7, 2010 for PCT/US2010/050701 claiming benefit of U.S. Appl. No. 12/571,969, filed Oct. 1, 2009.
International Search Report and Written Opinion mailed Jul. 31, 2009 for PCT/US2009/039578 claiming benefit of U.S. Appl. No. 12/103,834, filed Apr. 16, 2008.
International Search Report and Written Opinion mailed Jun. 10, 2010 for PCT/US2010/038177 claiming benefit of U.S. Appl. No. 12/483,807, filed Jun. 12, 2009.
International Search Report and Written Opinion mailed Jun. 4, 2010 for PCT/US2010/024073 filed Feb. 12, 2010, claiming benefit of U.S. Appl. No. 12/371,096, filed Feb. 13, 2009.
International Search Report and Written Opinion mailed May 9, 2011 for PCT/US2011/026412 claiming benefit of U.S. Appl. No. 12/872,663, filed Aug. 31, 2010.
International Search Report and Written Opinion mailed Oct. 5, 2010 for PCT/US2010/038845 claiming benefit of U.S. Appl. No. 12/486,992, filed Jun. 18, 2009.
Invitation to Pay Additional Fees mailed May 3, 2011 for PCT/US2011/026333 claiming benefit of U.S. Appl. No. 12/714,023, filed Feb. 26, 2010.
Invitation to Pay Additional Fees with Partial International Search mailed Nov. 26, 2009 for PCT/US2009/056670.
Kaus, Michael R., Ph.D., "Automated Segmentation of MR Images of Brain Tumors," Radiology, vol. 218, No. 2, (2001) pp. 586-591.
Kelly, Todd C., M.D., "Role of Navigation in Total Hip Arthroplasty." The Journal of Bone & Joint Surgery(2009) pp. 153-158. vol. 91-A, Supplement 1.
Klein, M., "Robot assisted insertion of craniofacial implants—clinical experience," CARS 2001, pp. 133-138 (2001) Elsevier Science B.V.
Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.
Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.
Murphy, S.B., et al. "The Hip Sextant: Navigation of Acetabular Component Orientation Using a Mechanical Instrument," brochure. (2009) 1 page.
Nicholls, Paul, M.D., "Trauma Grand Rounds PMI (Patient-Matched Implants)" brochure, Biomet Orthopedics, Inc., (Feb. 29, 2000) 1 page.
Overhoff, H.M., et al., "Total Knee Arthroplasty: Coordinate System Definition and Planning based on 3-D Ultrasound Image Volumes," CARS 2001, pp. 283-288, (2001) Elsevier Science B.V.
Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.
Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.
Portheine, K., "Development of a clinical demonstrator for computer assisted orthopedic surgery with CT-image based individual templates," Computer Assisted Radiology and Surgery, pp. 944-949, (1997) Elsevier Science B.V.
Radermacher, "Computer Assisted Orthopaedic Surgery with Image Based Individual Templates," Clinical Orthopaedics and Related Research No. 354, pp. 28-38 (1998) Lippincott Williams & Wilkins.
Radermacher, K., et al., "Computer Integrated Orthopaedic Surgery: Connection of Planning and Execution in Surgical Intervention," Computer-integrated surgery: technology and clinical applications, (1996) pp. 451-463.
Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.
Radermacher, K., et al., "Image Guided Orthopedic Surgery Using Individual Templates," Springer Berlin/Heidelberg, CVRMed-MRCAS'97, vol. 1205/1997 pp. 606-615).
Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.
Radermacher, Klaus, et al. "Computer Assisted Orthopaedic Individual Templates." Clinical Orthopaedics and Related Research. (Sep. 1998) No. 354; pp. 28-38.

(56) References Cited

OTHER PUBLICATIONS

Schuller-Götzburg, P., et al., 3D-Implantatplanung und Stereolithographie-Implantatbohrschablonen, Stomatologie 101.3, pp. 55-59 (2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (2007).

Slammin, John et al, "Do You Have This Implant in My Size?", MDT Medical Design Technology, 3 pages, http://www.mdtmag.com/scripts/ShowPR.asp?PUBCODE=046&ACCT=0007796&ISSUE . . . accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

International Search Report and Written Opinion for PCT/US2013/026875 mailed Jun. 7, 2013, claiming benefit of U.S. Appl. No. 13/400,652, filed Feb. 21, 2012.

International Preliminary Report on Patentability mailed Sep. 6, 2013 for PCT/US2012/026356 claiming benefit of U.S. Appl. No. 13/041,883, filed Mar. 7, 2011.

PATIENT-SPECIFIC PELVIC IMPLANTS FOR ACETABULAR RECONSTRUCTION

INTRODUCTION

The present teachings provide various patient-specific pelvic implants. The patient-specific pelvic implants can be spacers for revision acetabular implants used in acetabular reconstruction surgery, such as, for example, protrusio cages or acetabular cages that include an acetabular cup and one or more flanges coupled to the acetabular cup. The patient-specific spacers are prepared preoperatively for the specific patient based on medical scans of the relevant pelvic anatomy of the patient and are configured to be positioned under the flanges of the revision acetabular implants and register and mate with the corresponding pelvic anatomy of the patient in only one position.

SUMMARY

This section provides a general summary of the disclosure, and is not a comprehensive disclosure of its full scope or all of its features.

The present teachings provide a pelvic implant that includes a first surface and a patient-specific second surface opposite to the first surface. The first surface has a recess configured for receiving a portion of a flange of an acetabular cage. The patient-specific second surface is preoperatively configured from a three-dimensional digital image of a pelvis of a patient to mate and closely conform to a corresponding surface of the pelvis under the flange in only one position.

In some embodiments, the pelvic implant includes an acetabular cage having a flange and a patient-specific spacer. The patient-specific spacer has a first surface with a recess configured to receive a portion of the flange and a second surface opposite to the first surface. The second surface is patient-specific and preoperatively configured from a three-dimensional digital image of a pelvis of a patient to mate and closely conform as a negative to a corresponding surface of the pelvis under the flange in only one position.

The present teachings also provide a pelvic implant that includes an acetabular cage implantable into a pelvis of a patient and a plurality of patient-specific spacers. The acetabular cage includes an acetabular cup and a plurality of flanges coupled to the acetabular cup. Each spacer has a recess receiving a portion of a corresponding flange of the plurality of flanges and a patient-specific surface. The patient-specific surface is preoperatively configured from a three-dimensional digital image of the pelvis of the patient to mate and closely conform to a corresponding surface of the pelvis under the flange in only one position.

In some embodiments, the pelvic implant can include an acetabular cup and a patient-specific flange modularly coupled to the acetabular cup. The patient-specific flange has a patient-specific surface preoperatively configured from a three-dimensional digital image of the pelvis of the patient to mate and closely conform as a negative to a corresponding surface of the pelvis under the flange in only one position.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 2:
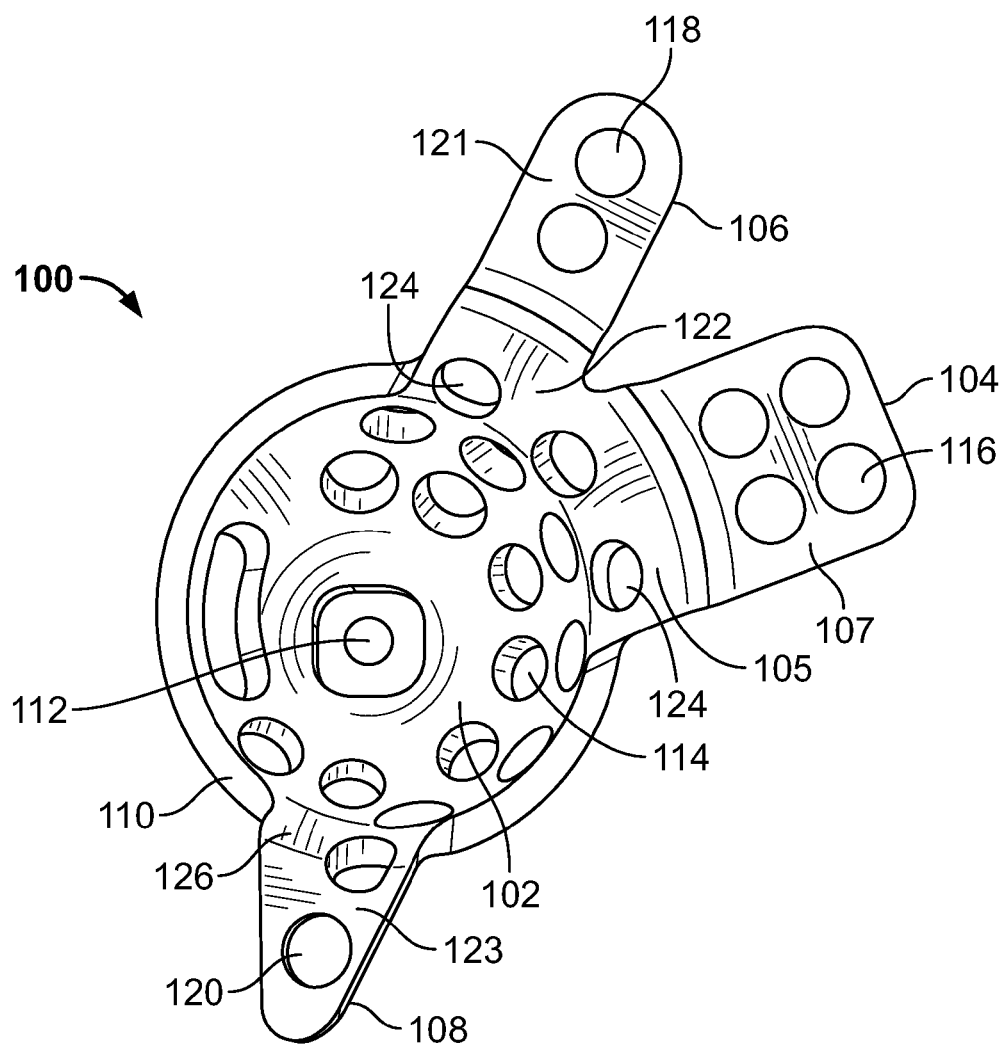
Figure 3A:
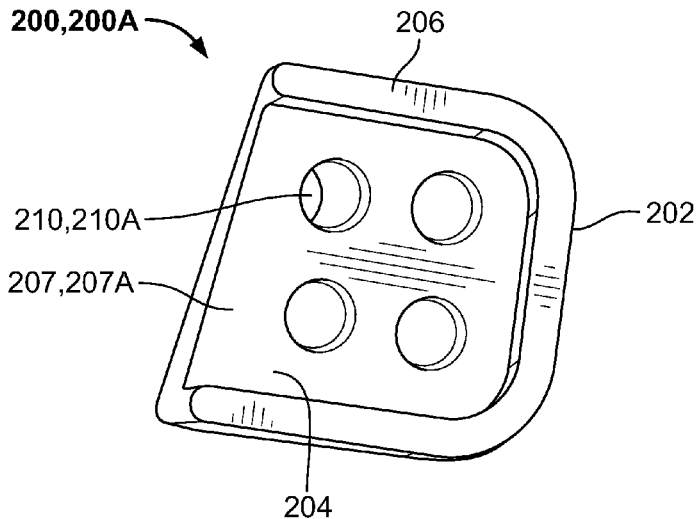
Figure 3B:
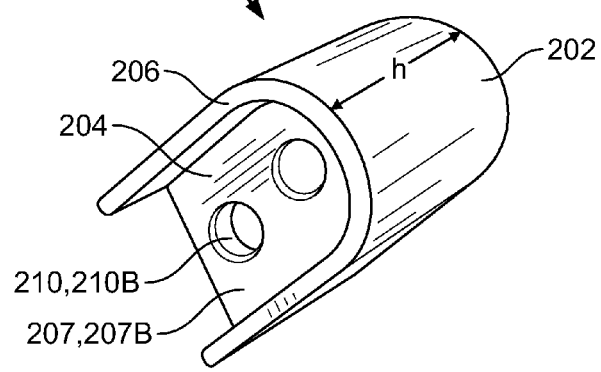
Figure 3C:
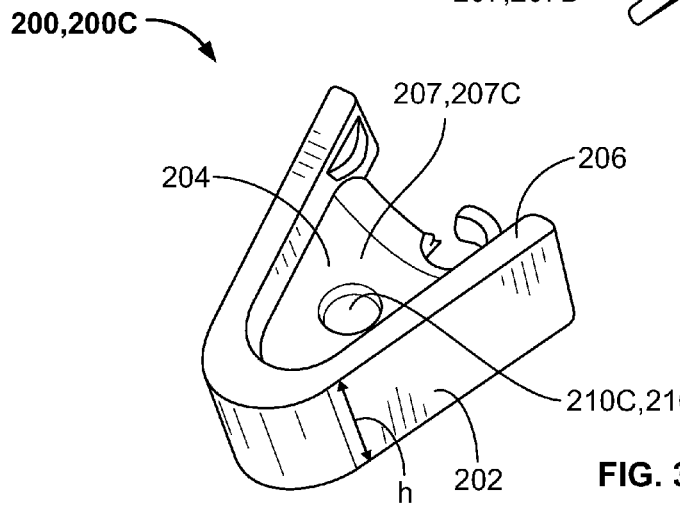
Figure 4A:
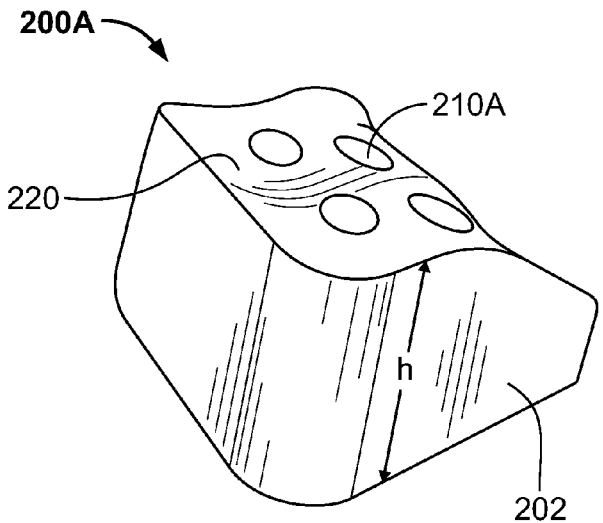
Figure 4B:
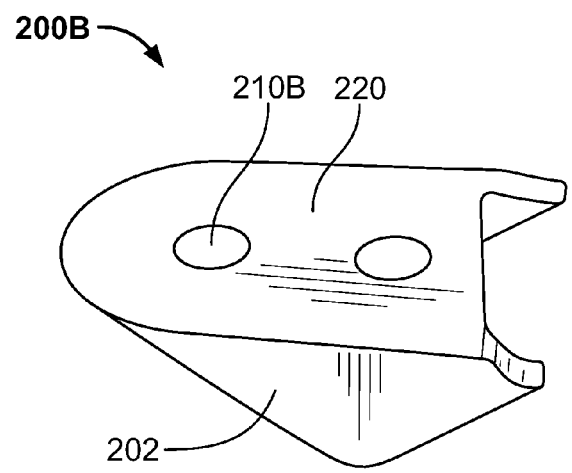
Figure 4C:
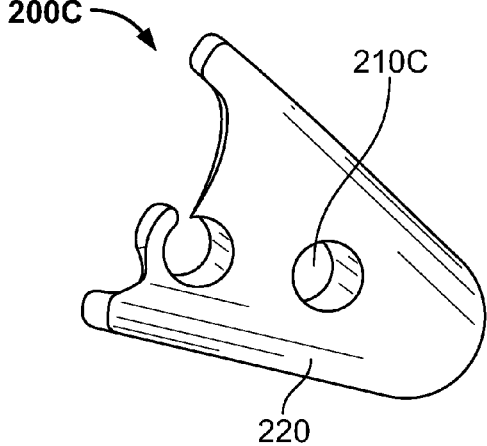
Figure 5:
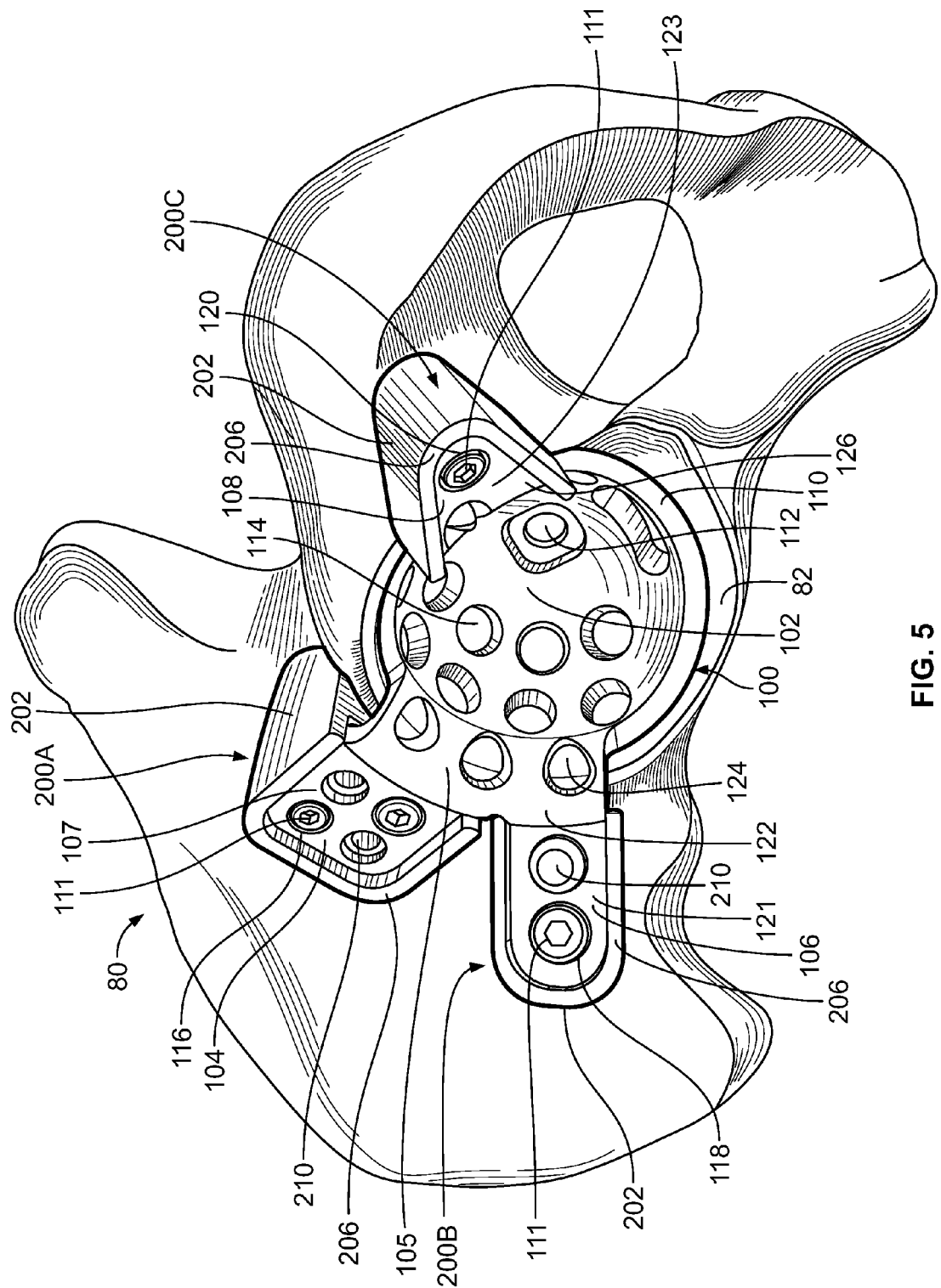
Figure 6:
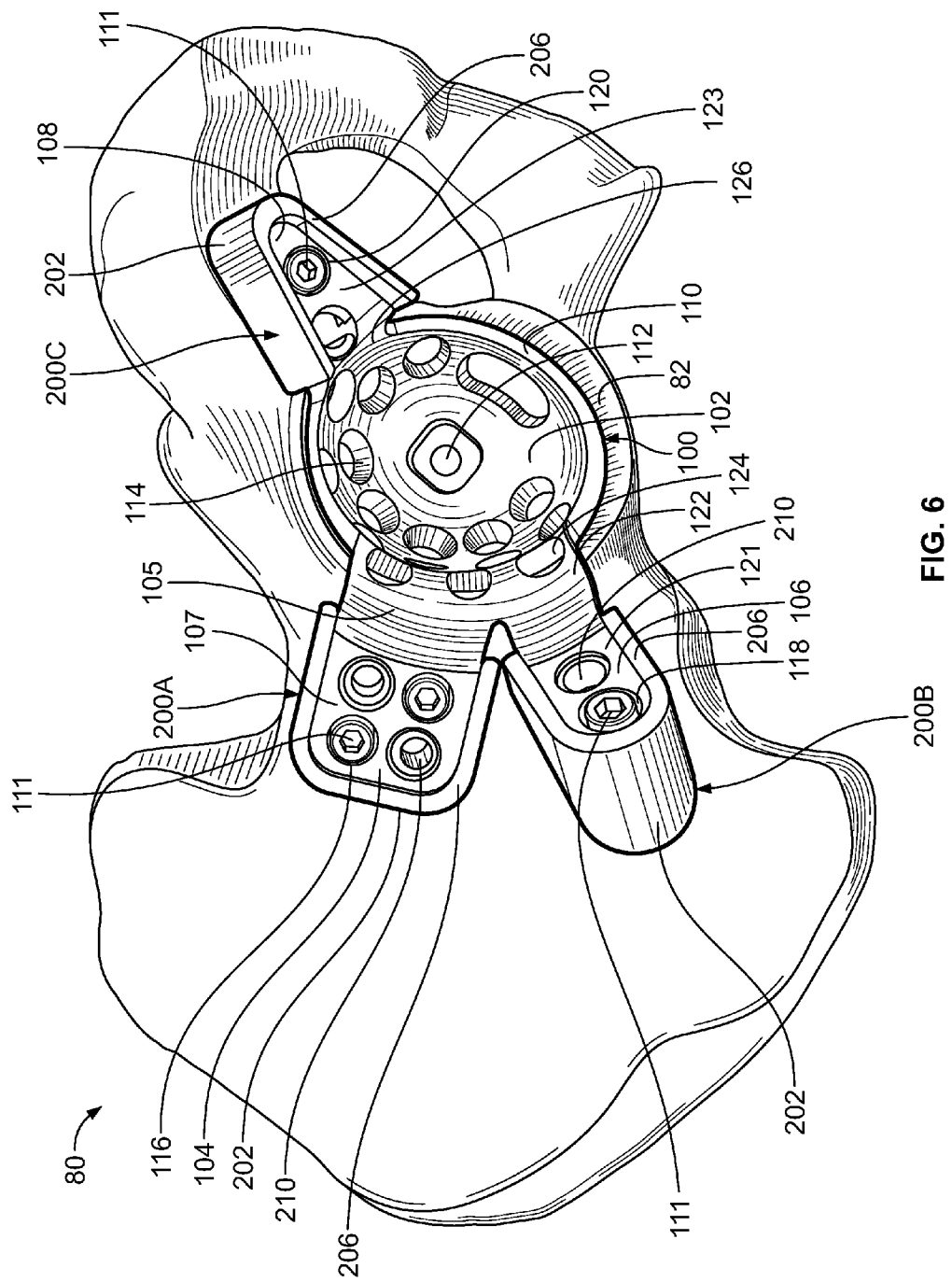
Figure 7:
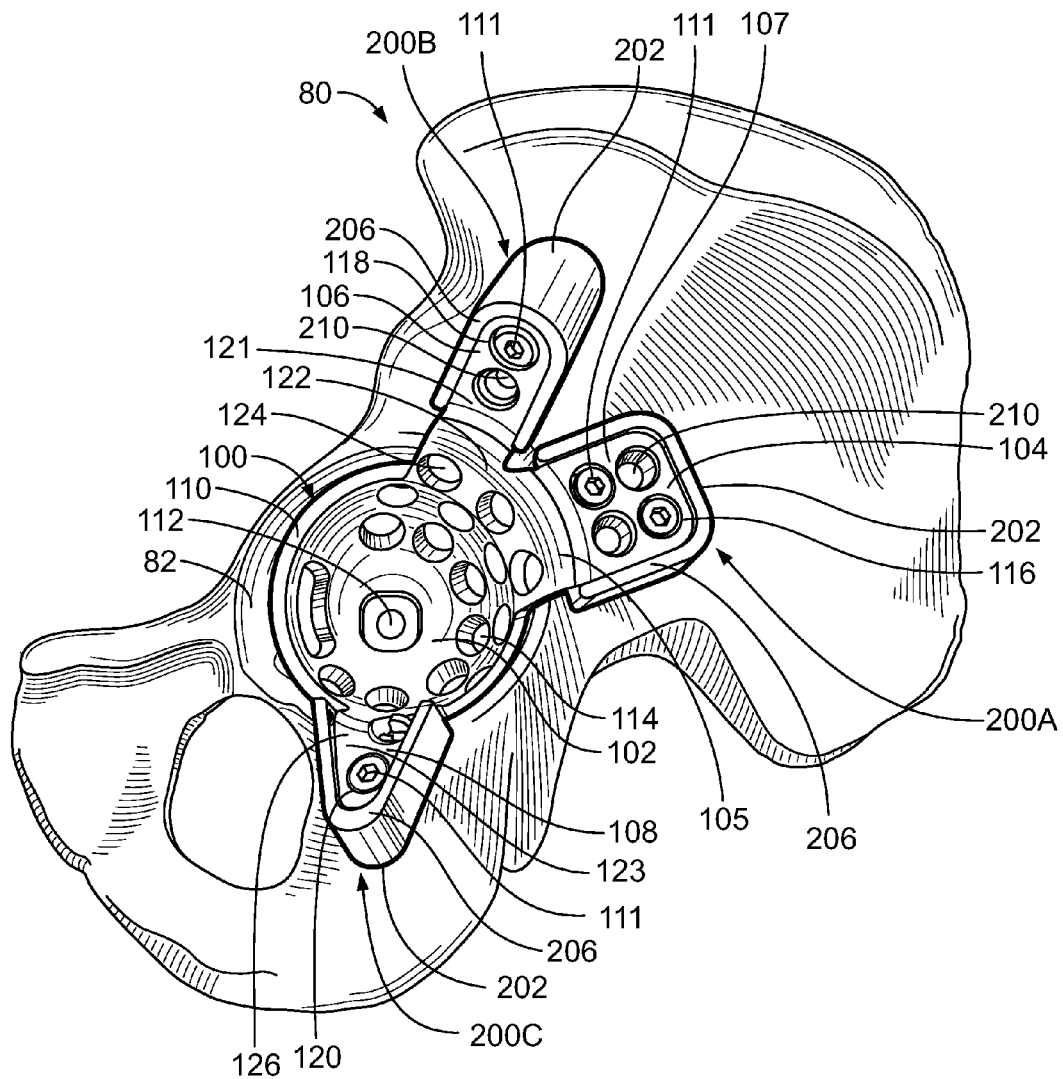
Figure 8:
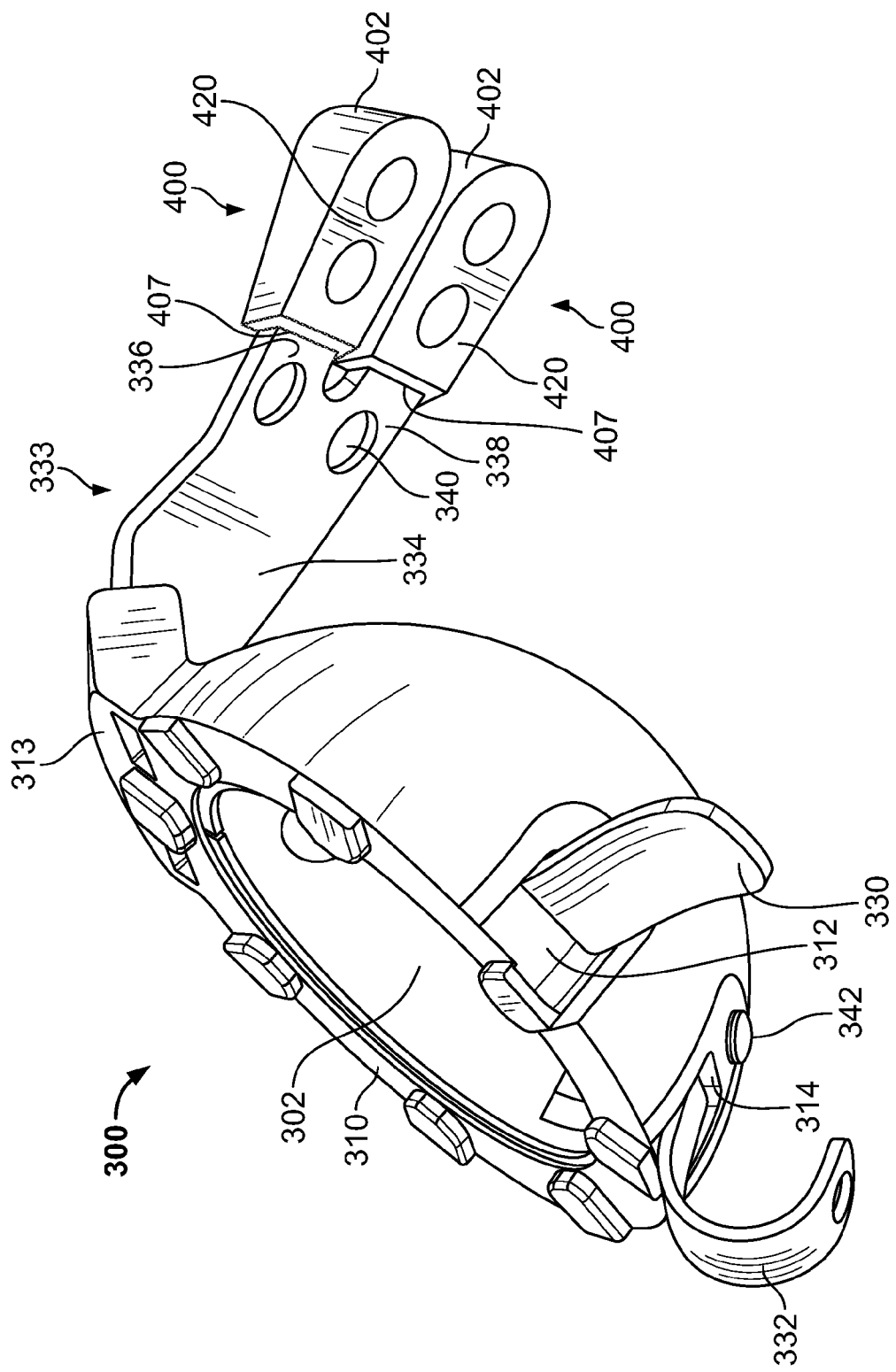
Figure 9:
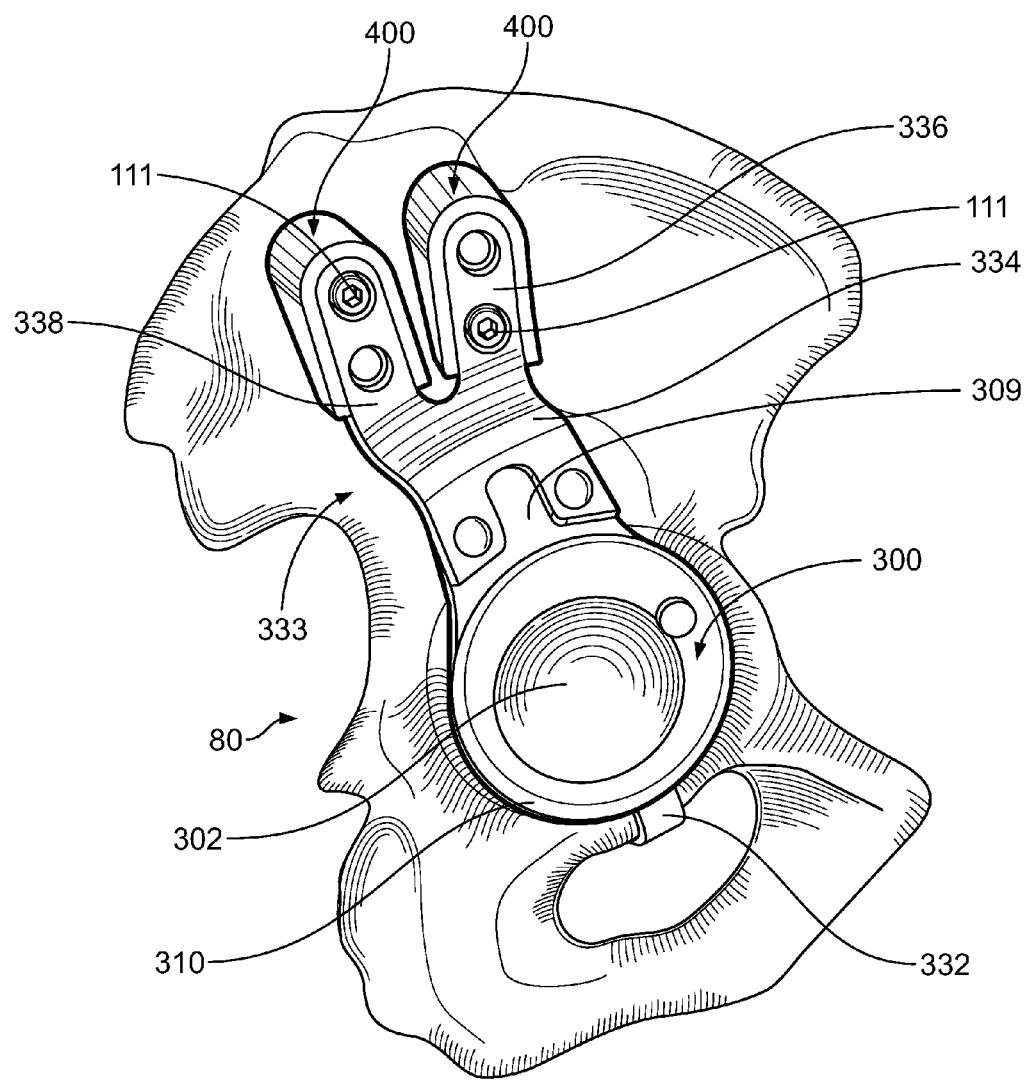
Figure 10:
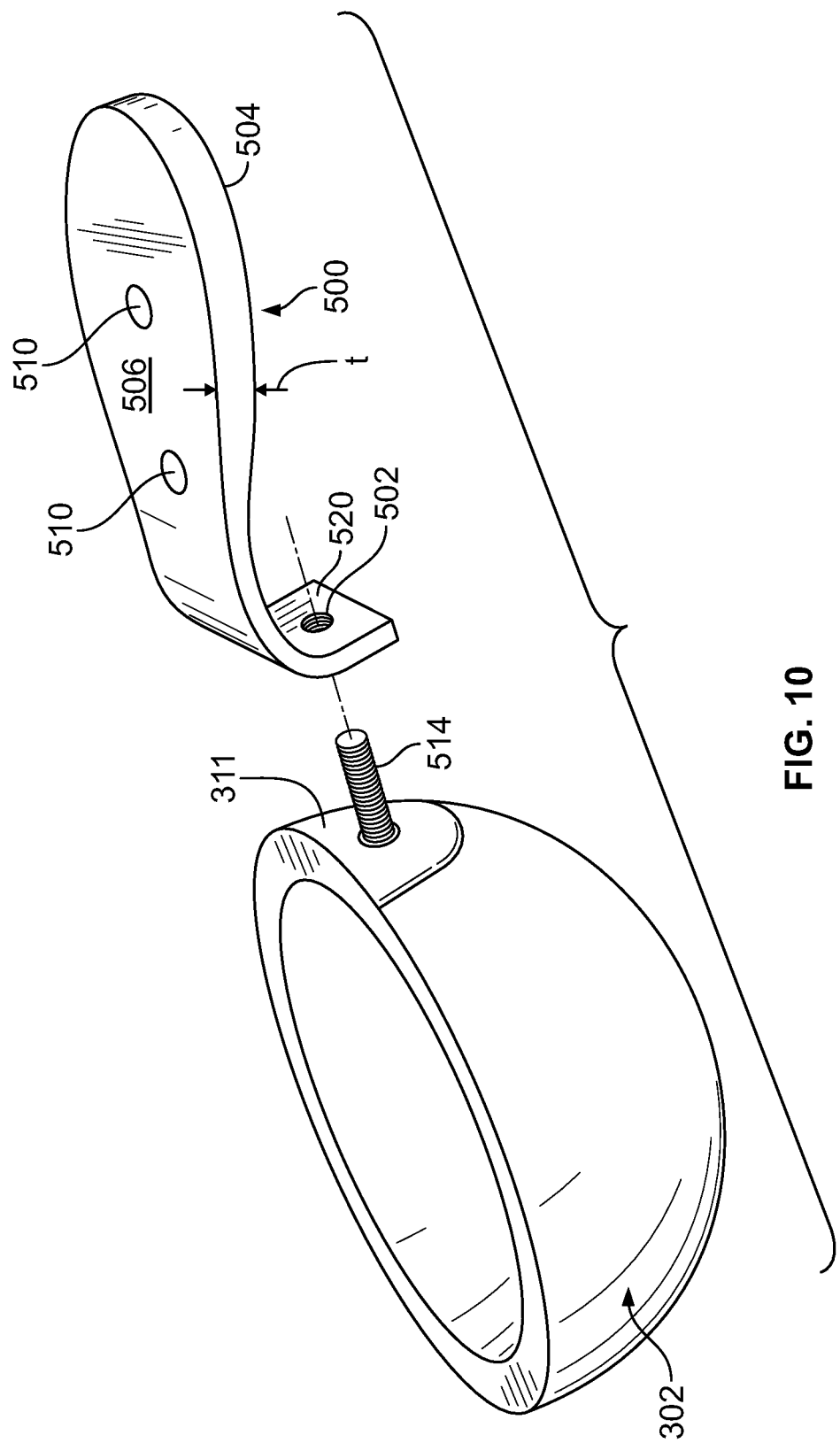

FIG. 1 is a perspective view of a pelvis of a patient;
FIG. 2 is a perspective view of an exemplary acetabular cage;
FIGS. 3A-3C are perspective views of patient-specific spacers for the acetabular cage of FIG. 2 according to the present teachings;
FIGS. 4A-4C are additional perspective views of the patient-specific spacers of FIGS. 3A-3C;
FIGS. 5-7 are different environmental perspective views of the spacers of FIGS. 3A-3C shown with the acetabular cage of FIG. 2 according to the present teachings;
FIG. 8 is a perspective view of another exemplary acetabular cage shown with patient-specific spacers according to the present teachings;
FIG. 9 is an environmental perspective view of the patient-specific spacers shown with the acetabular cage of FIG. 8 according to the present teachings; and
FIG. 10 is an exploded perspective view of an acetabular cup with a patient-specific flange according to the present teachings.

Corresponding reference numerals indicate corresponding parts throughout the several views of the drawings.

DETAILED DESCRIPTION

Exemplary embodiments will now be described more fully with reference to the accompanying drawings.

The present teachings generally provide patient-specific pelvic implants. The pelvic implants include patient-specific spacers for revision acetabular implants used in acetabular reconstruction surgery, including, for example, acetabular cages having acetabular cups with flanges or protrusio cages. The patient-specific spacers are prepared preoperatively for the specific patient based on medical scans of the relevant pelvic anatomy of the patient and positioned under the flanges of the revision acetabular implants.

Generally, patient-specific devices including implants and/or patient-specific instruments can be designed preoperatively using computer-assisted image methods based on three-dimensional images of the patient's joint anatomy reconstructed from MRI, CT, ultrasound, X-ray, or other medical scans of the patient's anatomy. Various CAD programs and/or software can be utilized for three-dimensional image reconstruction, such as, for example, software commercially available by Materialise USA, Plymouth, Mich.

Various pre-operative planning procedures are disclosed in commonly assigned and co-pending U.S. patent application Ser. No. 11/756,057, filed May 31, 2007, U.S. patent application Ser. No. 12/103,824, filed Apr. 16, 2008; U.S. patent application Ser. No. 12/371,096, filed Feb. 13, 2009, U.S. patent application Ser. No. 12/483,807, filed Jun. 12, 2009; U.S. patent application Ser. No. 12/872,663, filed Aug. 31, 2010, U.S. patent application Ser. No. 12/973,214, filed Dec. 20, 2010, and U.S. patent application Ser. No. 12/978,069, filed Dec. 23, 2010. The disclosures of the above applications are incorporated herein by reference.

In the preoperative planning stage for acetabular reconstruction, a preoperative surgical plan is formulated for a specific patient with interactive input from the patient's surgeon or other medical professional. Imaging data of the relevant anatomy of a patient can be obtained at a medical facility or doctor's office, using any of the medical imaging methods described above. The imaging data can include, for example, various medical scans of a relevant joint portion or other relevant portion of the patient's anatomy, as needed for joint or other anatomy modeling and, optionally, for determination of an implant alignment axis or for other alignment purposes. The imaging data thus obtained and other associated information can be used to construct a three-dimensional computer (digital) image of the joint or other portion of the anatomy of the patient, such as, in the present application, the patient's pelvis including the acetabular socket. The three-dimensional digital image of the patient's anatomy is used to formulate a preoperative surgical plan for the patient. The preoperative surgical plan includes the design and construction of implants and/or instruments according to selected methods of surgical preparation and implantation.

Generally, the patient-specific spacers and/or other patient-specific implants of the present teachings are configured to match the pelvic anatomy of a specific patient and are generally designed and configured using computer modeling based on the patient's reconstructed three-dimensional digital image of the patient's pelvic anatomy. The patient-specific implants have a pelvis engagement surface that is configured to conformingly contact and match a corresponding pelvic surface of the patient (with or without cartilage or other soft tissue), using the reconstructed three-dimensional digital image of the patient's pelvic anatomy and the computer methods discussed above. In this respect, a patient-specific implant can register and nestingly mate with the corresponding bone surface (with or without articular cartilage) of the specific patient in only one position.

In reconstructive or revision acetabular surgery, the old acetabular implant is removed from the pelvic bone or pelvis 80 and the acetabular area is prepared for a new acetabular implant. Soft tissue may be removed from the acetabular socket 82, from the acetabular rim 84 and from adjacent areas of the ilium 86, ischium 88 and pubic bone 90 (see FIG. 1). The pelvis 80 can be inspected for defects that will require the use of augments and other defect-correcting implants. The acetabular socket 82 can be reamed in preparation for receiving an acetabular cage (revision acetabular implant) that includes an acetabular cup (or shell or dome) with integral or modular flanges. An exemplary acetabular cage 100 is illustrated in FIG. 2. Various acetabular cages similar to the acetabular cage of FIG. 2 are commercially available from Biomet Manufacturing Corp., Warsaw, Ind. The acetabular cage 100 can include an acetabular cup 102 having a generally semi-spherical shape bounded by a cup rim 110.

The acetabular cage 100 is illustrated as having three flanges in this exemplary embodiment, although a different number of flanges and/or other hook or blade elements can be included. Referring to FIG. 2, first and second iliac flanges 104, 106 and an ischial flange 108 are illustrated. In this exemplary embodiment, the first iliac flange 104 has a first (proximal) portion 105 extending from the cup rim 110 and a second (distal) portion 107 that is square-like with four fixation holes 116 for fixation fasteners 111 (see FIG. 5) arranged to form a substantially square or square-like shape. The second iliac flange 106 has a first (proximal) portion 122 extending from the cup rim 110 and a second (distal) portion 121 that has an elongated rectangular shape with two fixation holes 118 arranged along the elongated rectangular shape. In some embodiments, the first portions 105 and 122 of the first and second iliac flanges 104, 106 can be continuous or unitary such that the first and second iliac flanges 104, 106 can be in the form of a single bifurcated iliac flange. The third or ischial flange 108 has a first (proximal) portion 126 extending from the cup rim 110 and a second (distal) portion 123 that has a triangular shape with two fixation holes 120. In the illustration of FIG. 2, the fixation holes 120 are oriented along one side of the second portion 123 and are offset from a centerline of the ischial flange 108. It will be appreciated, however, that the various fixation holes 116, 118, 120, their arrangements on the flanges 104, 106, 108 and the shapes and number of the flanges can vary for different acetabular cages 100.

The acetabular cup 102 can also include an apical hole 112 for coupling with an acetabular inserter. Various fixation holes 114 can be provided through the acetabular cup 102 for selective use with screws or other fixation fasteners by the surgeon. Fixation holes 124 for fixation fasteners can also be provided along the first portions 105, 122, 126 of the corresponding first, second and third flanges 104, 106, 108. The convex bone-engaging surface of the acetabular cup 102 can be coated with porous coating, such as a titanium alloy plasma spray porous coating commercially available from Biomet Manufacturing Corp., Warsaw, Ind.

Referring to FIGS. 3A, 3B and 3C (top side perspective views) and 4A, 4B and 4C (bottom side perspective views), exemplary embodiments of first, second and third patient-specific spacers (or shims) 200A, 200B, 200C (referenced collectively as 200) are illustrated. The patient-specific spacers 200A, 200B, 200C are configured for the first, second and third flanges 104, 106,108 and also for the underlying anatomy of the specific patient, as determined by the thee-dimensional digital image reconstruction of the pelvis of the patient from medical scans of the patient, as discussed above. More specifically, each patient-specific spacer 200A, 200B, 200C includes first and second opposing surfaces 204 and 220, a peripheral surface 202 between the first and second surfaces 204, 220 and various fixation holes 210 (or 210A, 210B, 210C) corresponding to the fixation holes of the respective flanges 104, 106, 108. The peripheral surface 202 forms an elevated ridge 206, such that the ridge 206 and the first surface 204 form a slot or recess 207 (collectively for 207A, 207B, 207C) for receiving a second portion of a corresponding flange 104, 106, 108, as discussed below.

Referring to FIGS. 3-7, the recess 207 of each patient-specific spacer 200A, 200B, 200C is configured during the preoperative plan to receive slidably or in a press-fit manner the second or distal portion 107, 121, 123 of the corresponding flange 104, 106, 108. In the exemplary illustrations, the recess 207A of the first spacer (or first iliac spacer) 200A is square-shaped to receive the second portion 107 of the first iliac flange 104. Similarly, the recess 207B of the second spacer (or second iliac spacer) 200B is shaped as an elongated rectangle to receive the second portion 121 of the second iliac flange 106. The recess 207C of the third spacer (or ischial spacer) 200C is shaped as a triangle to receive the second portion 126 of the ischial (third) flange 108.

With continued reference to FIGS. 3-7, the second surface 220 is a patient-specific bone-engaging surface that is configured during the preoperative plan to register in only one position and mate in a complementary manner (i.e., as a negative or mirror surface) to the iliac and ischial portions of the pelvis 80 that are under the corresponding iliac and ischial flanges 104, 106, 108., when the acetabular cage 100 is implanted. As can be seen in FIGS. 5-7, the patient-specific spacers 200 have a thickness h (i.e., height h of peripheral surface 202) that is substantially greater than the thickness of the flanges 104, 106, 108., although the thickness h can be variable depending on the pre-planned location of the spacer 200 relative to the pelvis 80. For example, in the embodiments of FIGS. 3-7, the first and second spacers 200A, 200B are iliac spacers and have a substantially variable thickness h, while the third spacer 200C is an ischial spacer and is shown with a substantially constant thickness. It should be appreciated, however that the thickness h of the spacers is also determined during the preoperative plan according to the anatomy of the specific patient and the surgeon-selected location for the flanges 104, 106, 108. Accordingly, the thickness h can vary in a patient-specific manner. Accordingly, the spacers 200 can provide reinforcement for the corresponding flanges 104, 106, 108. Further, the flanges 104, 106, 108 themselves can be configured with greater thickness and rigidity, because using their patient-specific spacers 200 makes it unnecessary to make the flanges 104, 106, 108 bend to engage the patient's pelvis 80. The acetabular cage 100 itself, including the location, number and shape of the various iliac and ischial flanges (such as flanges 104, 106, 108) in combination with the corresponding patient specific spacers 200 can be determined and selected during the preoperative plan based on the patient's anatomy and with surgeon input.

Computer instructions of tool paths for machining the patient-specific spacers 200 can be generated and stored in a tool path data file. The tool path can be provided as input to a CNC mill or other automated machining system, and the patient-specific spacers 200 can be machined from solid or porous metals and/or alloys. The patient-specific spacers 200 can also be manufactured from powder metal using rapid prototyping methods, such as, for example, stereolithography, laser deposition sintering or other such methods. The patient-specific spacers 200 can be sterilized and shipped to the surgeon or medical facility for use during the surgical procedure in a patient and surgeon specific kit. In addition to the patient-specific spacers 200, the kit can include the acetabular cage 100, an acetabular cup liner or other articulating bearing for the femoral head (not shown), various fixation screws and fasteners, various non-custom or patient-specific augments for the acetabular cup (dome) 102, as well as a selection of instruments generally used for the surgical procedure or specifically requested by the surgeon. The instruments in the kit can include an acetabular cup inserter and/or impactor, a reamer, various flange benders, vise grip instruments and other instruments for the surgical procedure, such as those commercially available from Biomet Manufacturing Corp., Warsaw, Ind. Patient-specific augments for the dome of the acetabular cup 102 are described in commonly assigned U.S. patent application Ser. No. 12/978,069, filed Dec. 23, 2010, the disclosure of which is incorporated herein by reference.

Referring to FIGS. 8 and 9, patient-specific spacers 400 can be similarly constructed for another exemplary acetabular cage 300 that is used in acetabular reconstruction. Acetabular cages similar to acetabular cage 300 are commercially available Biomet Manufacturing Corp., Warsaw, Ind. The acetabular cage 300 can include an acetabular cup or shell 302 having a cup rim 310, an ischial blade 330 extending from a first outer slot 312 of the acetabular cup 302, an obturator foramen hook 332 extending from a second outer slot 312 of the acetabular cup 302 and a bifurcated iliac flange 333 that includes a common first (proximal) portion 334 extending from the cup rim 310 and first and second distal flange portions 336, 338 extending from the common first portion 334. In this embodiment of the acetabular cage 300, the ischial blade 330, the obturator foramen hook 332 and the bifurcated iliac flange 333 are removably coupled to the acetabular cup 302 by snap-fit and/or by using, for example, screws or other fasteners and are selectively included in the prosthesis at the discretion of the surgeon. For example, in the environmental view of FIG. 9 only the bifurcated iliac flange 333 and the obturator foramen hook 332 are shown. An exemplary fastener 342 coupling the obturator foramen hook 332 to the acetabular cup 302 is shown in the view of FIG. 8 and a similar fastener can be used for the ischial blade 330 (hidden from view). The first portion 334 of the bifurcated iliac flange 333 can also be attached with fasteners to a corresponding extension 309 of the cup rim 310.

The acetabular cup 302 and the ischial blade 330 can be made from a titanium alloy (such as Ti-6Al-4V, for example). The convex (bone-engaging surface of the acetabular cup 302 can be coated with porous coating, such as a titanium alloy plasma spray porous coating commercially available from Biomet Manufacturing Corp., Warsaw, Ind. The obturator foramen hook 332 and the bifurcated iliac flange 333 can be made from pure titanium or other metal. The obturator foramen hook 332 can be crimped by the surgeon during implantation. The bifurcated iliac flange 333 can also be bent during implantation. In other embodiments, the bifurcated iliac flange 333 can also be made of titanium alloy and have a greater thickness when used with the patient-specific spacers 400 because, as discussed above in connection with the spacers 200, each patient-specific spacer 400 is also designed preoperatively to register in only one position and nestingly mate (as a negative) with the underlying iliac surface of the specific patient and provide rigidity and support on the corresponding iliac surface without the need to bend the iliac flange 333. Apart from the fact that the spacers 400 are designed to receive the corresponding first and second distal flange portions 336, 338 of the bifurcated iliac flange 333, the spacers 400 are similar to the spacers 200 and the description of similar features is not repeated. For example, each patient-specific spacer 400 has a recess 407 that receives a corresponding distal iliac flange portion 336, 338 and an opposite patient-specific surface 420 configured during the preoperative plan to mate to a corresponding iliac anatomy of the pelvis 80 of the patient and register in only one position.

In some embodiments, an entire flange can be preoperatively designed to be patient-specific to nestingly conform to the specific patient's periacetabular anatomy in a single position, without the need of intraoperative bending or other deformation by the surgeon. In this respect, the patient-specific flange can be designed with adequate thickness for stability and rigidity and without using any spacers. An exemplary patient-specific flange 500 is illustrated in FIG. 10. The patient-specific flange 500 can be modularly or removably connected to an acetabular cup 302 (shown generically). In some embodiments, the patient-specific flange 500 can have a connecting portion 520 with an opening 502 for receiving a fastener 514 from a corresponding connecting portion 311 of the acetabular cup 311, although other types of modular connectors can be used, such as tongue-and-groove with or without screws, etc.

The patient-specific flange 500 has first and second opposing surfaces 504, 506. The first surface 504 is configured as a patient-specific surface that mirrors (as a negative surface) the corresponding pelvic anatomy of the patient. Accordingly, the width or thickness "t" of the flange between the first and second surfaces 540, 506 can be variable in a patient-specific manner. The patient-specific flange 500 is shown generically with two fixation holes 510, although it will be appreciated that the patient-specific flange 500 can be designed with different number of and arrangement of fixation holes and overall shape. The modular patient-specific flange 500 can be used in an acetabular cage (100, 300) that includes additional non custom flanges and patient-specific spacers (200, 400) for the non-custom flanges, as described above. In this respect, the patient-specific flange 500 can replace one of the non-custom flanges of the acetabular cage Summarizing, the present teachings provide various patient-specific spacers 200, 400 that can be included in a kit for acetabular revision surgery for a specific patient. The patient-specific spacers 200, 400 are designed during a preoperative surgical plan of the patient based on a three dimensional digital image of the pelvic anatomy of the patient that is constructed using commercially available software from medical scans of the patient. The design and construction of the patient-specific spacers 200, 400 are made preoperatively in conjunction with the selection of an appropriate acetabular cage for the patient. A plurality of patient-specific spacers 200, 400 can be included in the kit. The patient-specific spacers 200, 400 combine patient-specific customization with rigidity and reinforcement for the flanges of the acetabular cage and can relieve the surgeon from the need to bend corresponding flanges of the acetabular cages intraoperatively for engagement with the pelvis of the specific patient. In this respect, the patient-specific spacers can facilitate and possibly streamline some acetabular reconstruction procedures. In some embodiments, modular patient-specific flanges for use without spacers can also be included in the kit.

Example embodiments are provided so that this disclosure is thorough, and fully conveys the scope to those who are skilled in the art. Numerous specific details are set forth such as examples of specific components, devices, and methods, to provide a thorough understanding of embodiments of the present disclosure.

It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. Accordingly, individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of making a pelvic implant comprising:
   using a three-dimensional digital image of said pelvis of the patient measuring patient-specific anatomical features of the pelvis of the patient;
   customizing an acetabular cage implantable into a pelvis of a patient; the acetabular cage including an acetabular cup and a plurality of flanges couplable to an upper portion of the acetabular cup; and
   customizing a plurality of patient-specific spacers, wherein each patient-specific spacer comprises a first surface and opposed and second surface, and a peripheral surface located between the first and second surfaces, wherein the first surface has a recess receiving a complementary-shaped portion of a corresponding flange of the plurality of flanges, wherein the second surface defines a patient-specific bone-engaging surface preoperatively configured from the three-dimensional digital image of the pelvis of the patient to complementary mate and closely conform to mirror a corresponding surface of the pelvis under the flange in only one position,
   wherein the peripheral surface includes a ridge surrounding the recess that is elevated relative to the first surface,
   wherein each patient-specific spacer of the plurality of patient-specific spacers have a selected shape and each shape corresponds to the complementary-shaped of the corresponding flange,
   wherein at least one flange of the plurality of flanges includes an iliac flange and at least one patient-specific spacer of the plurality of patient-specific spacers includes an iliac spacer couplable to the iliac flange.

2. The method of claim 1, wherein customizing the plurality of patient-specific spacers including forming a recess of the iliac spacer to have an elongated rectangular shape.

3. The method of claim 1, wherein customizing the plurality of patient-specific spacers including forming a recess of the iliac spacer to have a square shape.

4. The method of claim 1, wherein customizing the acetabular cage includes providing the plurality of flanges to include an ischial flange couplable to the upper portion of the acetabular cup.

5. The method of claim 4, wherein customizing the plurality of patient-specific spacers includes providing an ischial flange having a recess that is a triangular shape.

6. The method of claim 1, further comprising:
   providing an ischial flange as one of the plurality of flanges; and
   providing an ischial spacer as one of the plurality of patient-specific spacers.

7. The method of claim 1, further comprising:
   providing at least one flange of the plurality of flanges to be removably couplable to the acetabular acetabular cup.

8. The method of claim 1, further comprising:
   providing an ischial blade modularly couplable to the acetabular cup.

9. The method of claim 1, further comprising:
   providing an obturator foramen hook modularly couplable to the acetabular cup.

10. The method of claim 1, wherein at least one patient-specific spacer has variable thickness.

11. The method of claim 1, wherein customizing the plurality of patient-specific spacers includes providing a varied thickness among the plurality of patient-specific spacers.

12. The method of claim 11, wherein customizing the acetabular cage includes providing at least one of flanges of the plurality of flanges to engage the outer slot.

13. The method of claim 1, wherein customizing the acetabular cage includes forming at least one outer slot in the acetabular cup.

14. The method of claim 1, further comprising:
   forming a bore into the patient-specific spacers.

* * * * *